(12) United States Patent
Hoffman

(10) Patent No.: US 6,425,255 B1
(45) Date of Patent: Jul. 30, 2002

(54) SUITCASE COOLING APPARATUS

(76) Inventor: Karl Hoffman, 35 Tradewinds Cir., Tequesta, FL (US) 33469

( * ) Notice: Subject to any disclaimer, the term of this patent is extended or adjusted under 35 U.S.C. 154(b) by 0 days.

(21) Appl. No.: 09/749,182

(22) Filed: Dec. 26, 2000

(51) Int. Cl.[7] .............................................. F25D 23/12
(52) U.S. Cl. ........................ 62/261; 165/47; 128/205.26
(58) Field of Search .............................. 62/261, 259.3, 62/457.1; 165/46, 47; 5/421, 423; 128/205.26, 204.15

(56) References Cited

U.S. PATENT DOCUMENTS

| | | | |
|---|---|---|---|
| 2,695,413 A | * | 11/1954 | Maat |
| 3,404,684 A | * | 10/1968 | Brewer, Jr. et al. |
| 3,713,182 A | * | 1/1973 | McNeal |
| 3,802,216 A | * | 4/1974 | Brandimarte |
| 3,991,819 A | * | 11/1976 | Clark |
| 4,064,835 A | | 12/1977 | Rabenbauer |
| 4,132,262 A | | 1/1979 | Wibell |
| 4,388,738 A | | 6/1983 | Wagner |
| 4,602,486 A | * | 7/1986 | Weinstein ................... 62/261 |
| 4,773,310 A | * | 9/1988 | Corwin |
| 4,888,958 A | * | 12/1989 | Ella |
| 5,125,238 A | | 6/1992 | Ragan et al. |
| 5,165,127 A | | 11/1992 | Nicholson |
| 5,632,051 A | | 5/1997 | Stanley et al. |
| 5,964,222 A | * | 10/1999 | Kotliar ................... 128/205.26 |
| 6,167,714 B1 | * | 1/2001 | Baffes |

FOREIGN PATENT DOCUMENTS

| | | | |
|---|---|---|---|
| JP | 62056719 A | * | 3/1987 |
| JP | 02096059 A | * | 4/1990 |

* cited by examiner

Primary Examiner—Chen-Wen Jiang
(74) Attorney, Agent, or Firm—McHale & Slavin, P.A.

(57) ABSTRACT

The instant invention is a lightweight, hand portable air conditioner or heater with an attachment that encloses a small area thus permitting the enclosed are to be heated or cooled. The apparatus has a housing unit with wheels and a handle for pulling or pushing the unit. The top of the unit has two telescopic extension poles that can be extended the length of a bed. A suitable material placed over the extended V shaped poles creates a small enclosure for a person. The housing unit contains a compressor with a refrigerant, two fans operated by a central motor, and a cool portion and hot portion. The compressor will cool the refrigerant by compressing the gas to liquid, the cool liquid will be diverted to the cool portion and a fan will direct the cool air out of the housing unit through a vent and into the enclosed area created by the material draped over the extended poles. As a result, the enclosed area can be cooled allowing a person inside to rest or sleep comfortably.

11 Claims, 2 Drawing Sheets

SUITCASE COOLING APPARATUS

FIELD OF THE INVENTION

This invention relates generally to air conditioning and more particularly to a portable cooling unit that cools, or heats, a small area.

BACKGROUND OF THE INVENTION

In today's modern world, travelers, for business or pleasure, may easily find themselves in a sleeping situation that does not meet the comforts available in their own residence. For instance, residents from the northern states of the United States may find sleeping in the Caribbeans a most uncomfortable experience if air conditioning is not available. However, if many such areas air conditioning is not available for the local residents believe the ocean breeze is sufficient. This could quickly spoil a vacation or business trip for the unsuspecting visitor.

Opening a window is often not helpful because various bugs such as mosquitos, moths, and gnats may then enter the room providing further disruptions from sleep. Additionally, the traveler may be disturbed by outside noises, further disturbing their sleep.

Lack of sleep may cause, among other symptoms, irritability and decreased concentration. A person experiencing these symptoms may not be in peak form while conducting a business deal or may not enjoy their travels. Thus, what is lacking in the art is a means for cooling a small sleeping area that is lightweight, portable, and requires low voltage making it inexpensive to operate and suitable for use in most any environment.

DESCRIPTION OF THE PRIOR ART

Air conditioning units have been used in the prior art to provide fixed and portable cooling of enclosed spaces. U.S. Pat. Nos. 4,132,262; 5,165,127; 5,125,238; 4,064,835; 5,632,051 and 4,388,738 all disclose various permutations of heating and cooling blankets or mattress utilizing fluid or air means for transferring heat away from a body in contact with the blanket or mattress or directing cool air onto a body in contact by channels placed throughout the blanket or mattress fabric.

The prior art of the first class is generally limited by the temporary cooling capacity of the coolants and by the necessity of and efforts associated with transferring said coolants to the air-conditioning units on a regular basis to maintain cooling capacity. Said maintenance necessitates the use of auxiliary devices, such as conventional freezer units to charge said coolants, which may be bulky, stationary, and costly.

The prior art of the second class is generally limited in size to a bed-size mattress or blanket requiring physical contact with the end user to accomplish its objective. Such contact may be physically impracticable due to a variety of medical conditions and the subject's movement is considerably restricted. Further, the use of a blanket prevents observation of a subject, if desired and the use of a mattress may require the concomitant use of a blanket or other means for containing the cool environment to promote efficiency of use.

SUMMARY OF THE INVENTION

The instant invention is a lightweight, hand portable air conditioner with an attachment that encloses a small area such as a bed. The housing unit is defined by a top surface, a bottom surface, four sides, and an inner cavity. Within two opposing sides of the four sides are vents. The housing unit is approximately the size of a medium rectangular suitcase and has at least one wheel, preferably four, so that it can be pulled or pushed by a traveler in the same manner travelers transport their suitcases through airports. The housing unit has a flat top upon which the traveler may place other luggage.

Residing along the top sides are two, one along each side, hollow poles. The hollow poles are of the telescopic extension type, i.e. when not in use, the hollow poles are of minutely smaller diameters with sections of a set length that fit inside of each other such that when in use, the pole will extend the length of the number of sections. When extended, the poles will be similar to a V-shape with the closed end of the V originating from the top surface of the housing unit and the open end of the V extending outward therefrom. If the housing unit is placed at the end of a bed, the extended poles will reach to the head of the bed. The poles can then be draped with a suitable material thus forming an enclosure for a sleeping traveler.

In the preferred embodiment, the housing unit will have two stabilizers, one on opposite sides of two of the four sides of the housing unit. The stabilizers will pivot from an upward angle to a downward angle such that the housing unit is securely anchored when in use or storage. Preferably, the housing unit will also have a handle at one end for the traveler to use for pulling or pushing the unit.

The cavity will house a compressor, two propeller fans operated by a central motor, and two hoses. The two hoses extend from the compressor with a first hose extending to a heat portion side of the cavity and a second hose extending to a cool portion side of the cavity. Both the heat portion side and the cool portion side are directly in front of the vents within the two sides of the housing unit. The motor is between the two propeller fans and there is a fan in front of the heat portion side and the cool portion side.

In operation, the compressor takes a compressible cooling fluid known as a refrigerant and compresses the gas from into a liquid form. The cooled liquid refrigerant will pass through the second hose to a coil in the cool portion side of the cavity. The coil will be cooled by the expanding refrigerant gas. The propeller fan, operated by the central motor in a conventional manner well known in the art, will blow the cooled air through the vent in the side of the housing unit into the enclosure provided by the suitable material draped over the extended poles. The warmed refrigerant gas will return to the compressor through a conduit. As a result, a sleeping traveler within the enclosure will stay cool and comfortable all night.

Accordingly, it is an objective of the instant invention to disclose a lightweight, portable cooling/heating unit.

It is a further objective of the instant invention to disclose an inexpensive cooling/heating unit.

It is yet another objective of the instant invention to disclose a method for cooling or heating a small enclosed area.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE INVENTION

Figure 1:
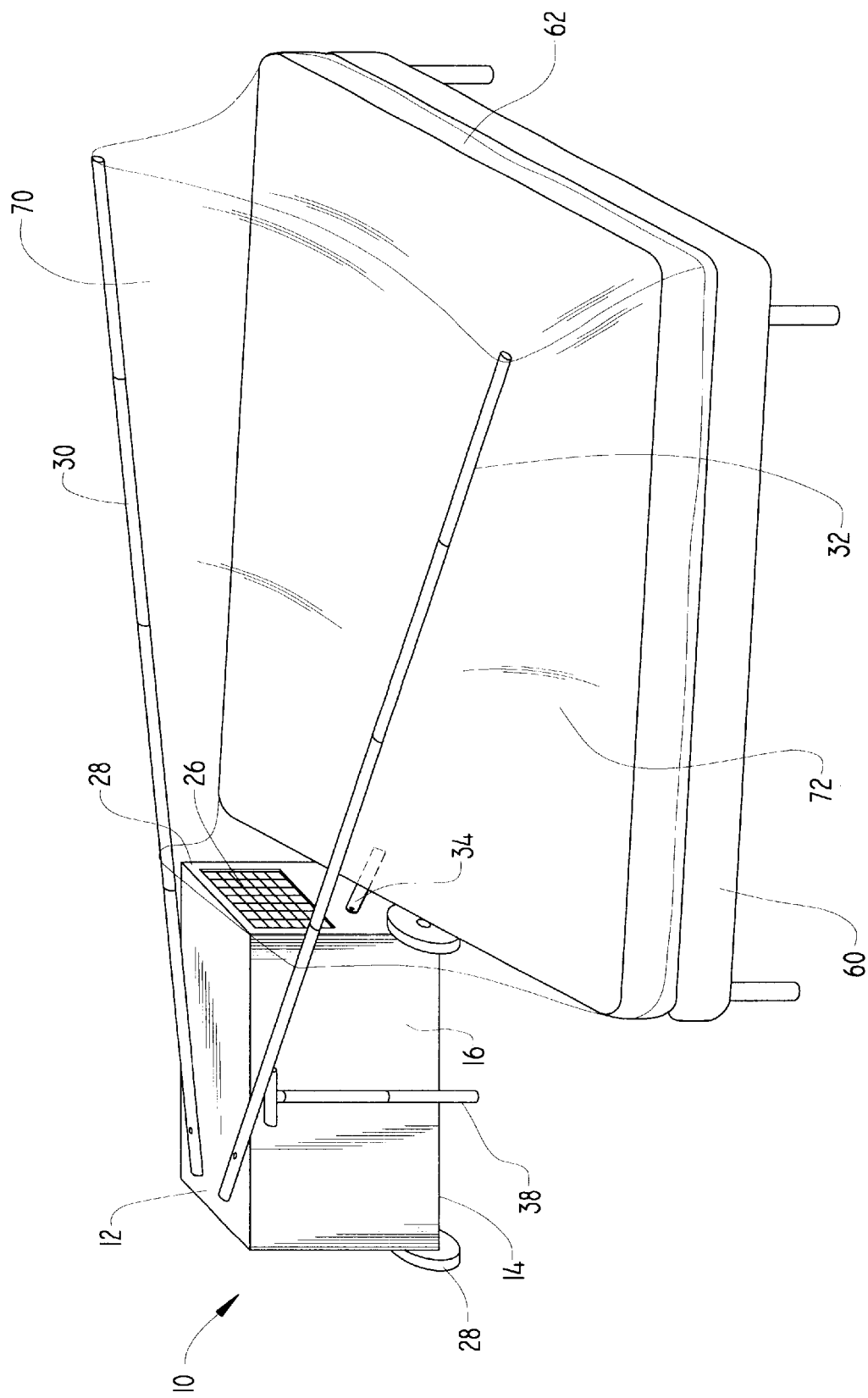
FIG. 1 is a pictorial view of the instant invention in use enclosing a bed.

The instant invention is a lightweight, hand portable cooling or heating unit with an attachment that encloses a small area such as a bed. Now referring to FIGS. 1 and 3, the housing unit 10 is defined by a top surface 12, a bottom surface 14, four sides 16, 18 (shown), 20, and 22 (not shown), and an inner cavity 24. At a convenient place on the housing unit is an electrical cord for providing electricity. Within two opposite sides of the four sides are two vents 26 and 27. The housing unit 10 has at least one wheel 28 and in the preferred embodiment has four wheels, one at each corner as shown. The wheels 28 permit the housing unit 10 to be easily pulled or pushed by a traveler.

Figure 3:
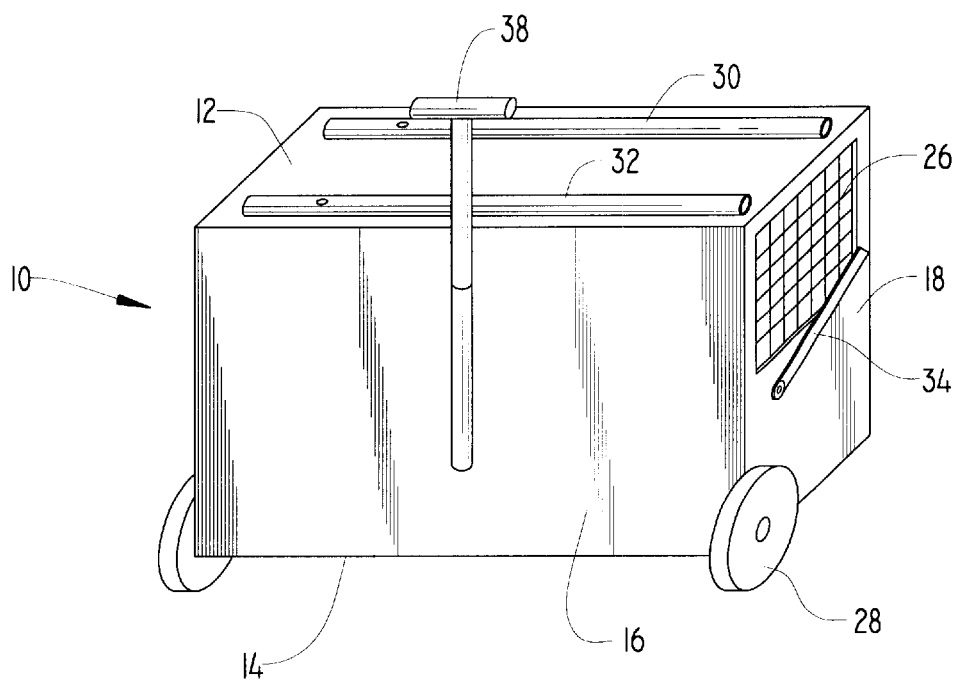
FIG. 3 is a pictorial view of the instant invention when no being used.

Residing along the top side 12 of the housing unit 10 are two poles 30 and 32 respectively. The poles 30 and 32 are of the telescopic extension type. As depicted in FIG. 3, when not in use, the poles 30 and 32 are of minutely smaller sections of a set length that fit inside of each other such that when in use, the pole will extend the length of the number of sections. When extended, as depicted in FIG. 1, the poles 30 and 32 will be similar to a V-shape with the closed end of the V originating from the housing unit 10 and the open end of the V extending outward therefrom. If the housing unit 10 is placed at the end of a bed 60, the extended poles will reach to the head of the bed 62. The poles 30 and 32 can then be draped with a suitable material 70 thus forming an enclosure 72 for a sleeping traveler.

In the preferred embodiment, the housing unit 10 will have two stabilizers 34(shown) and 36 (not shown). The stabilizers 34 and 36 will pivot from an upward angle to a downward angle to securely anchored the housing unit 10 when in use or during storage. Preferably, the housing unit 10 will also have a handle 38 at one end for the traveler to use for pulling or pushing the unit.

Figure 2:
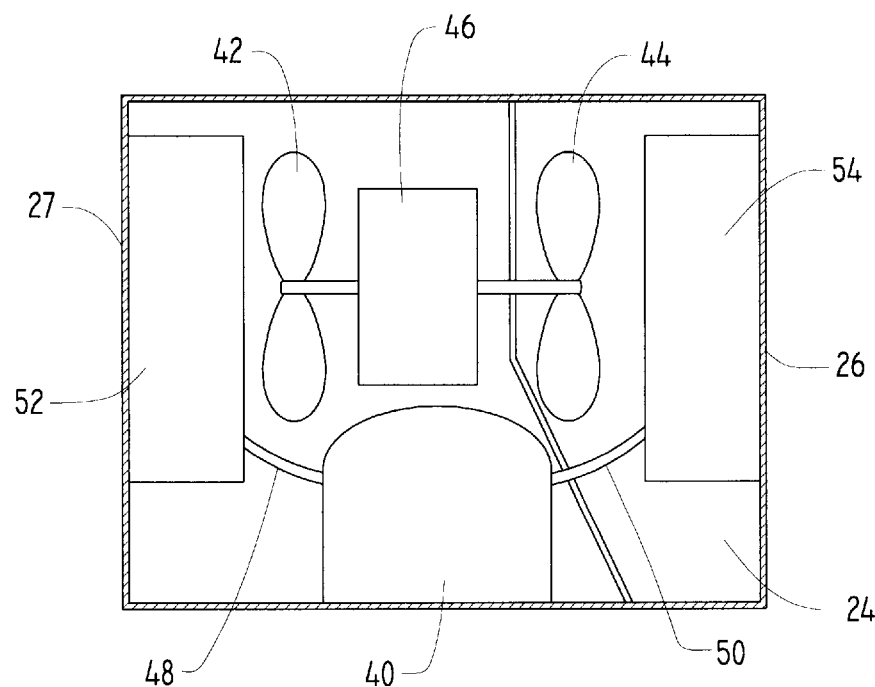
FIG. 2 is a internal view of the cavity of the housing unit of the instant invention.

Now referring to FIG. 2, the cavity 24 will house a compressor 40, two propeller fans 42 and 44 operated by a central motor 46, and two hoses 48 and 50. The two hoses 48 and 50 extend from the compressor 40 with a first hose 48 extending to a heat portion side 52 of the cavity 24 and a second hose 50 extending to a cool portion side 54 of the cavity 24. Both the heat portion side 52 and the cool portion side 54 are directly in front of the vents 26 and 27 within the two sides of the housing unit 10. The motor 46 is between the two propeller fans 42 and 44 and there is a fan in front of the heat portion side 52 and the cool portions side 54.

In operation, the compressor 40 takes a compressible cooling fluid such as environmentally friendly 134A refrigerant for example DuPont's SUVA HFC-134a (a trademark for 1,1,1,2-tetrafluoro-ethane used as a refrigerant) and compresses the gas into a liquid form. A linear compressor is a positive displacement compressors in which the piston is driven by a linear motor which produces force in line with the piston movement so there is no need for conversion of force from one direction to another. This substantially reduces the bearing load and friction losses, resulting in higher efficiencies than conventional compressors. By way of example, linear compressors MCI 929, MCI1129F, and MCI 1129C of the KOOLINEAR compressor line, manufactured by Micro Compressors International, Ltd., are designed to run using D.C. power and suitable for small mobile applications. The KOOLINEAR compressors handle up to 80 watts at 12 or 24 volts and also adhere to ISO7637-1 and IS7637-2 standards.

The cooled liquid SUVA will pass through the second hose 50 to a coil in the cool portion side 52 of the cavity 24. The coil will be cooled by the expanding SUVA gas. A conventional thermostat will be located will be located at some convenient point in the housing unit. The propeller fan 44, operated by the central motor 46 in a conventional manner well known in the art, will blow the cooled air through the vent 27 in the side of the housing unit 10 into the enclosure 72 provided by the suitable material 70 draped over the extended poles 30 and 32. The warmed FREON gas will return to the compressor 40 through a conduit. As a result, a sleeping traveler within the enclosure 70 will stay cool and comfortable all night.

Thus, the portable air conditioner of the instant invention employs a housing unit defined as a suitcase enclosure having an outer surface and an inner surface forming a cavity therein. A discharge port having an inner side surface and an outer side surface provides a first passageway from the cavity. A return air port provides a second passageway from the outer surface into the cavity. The air conditioning unit is mounted in the cavity and fluidly coupled to the discharge port for discharging conditioned air. An electrical cord is electrically coupled to the air conditioning unit and releasably coupled to an external power supply for operation of the air conditioning unit, the electrical cord may be made retractable for ease of transport.

The attachment means is securable to the outer side surface of the discharge port and is formed from the flexible sheet of mater for covering a spacial area for directed distribution of conditioned air.

The conditioned air is cooled or heated, depending upon the preference of the individual. A propeller fan can be made reversable allowing ease of connection thereby allowing the ports to be reversed for the heating/cooling process.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

What is claimed is:

1. A portable suitcase air conditioner comprising:

a suitcase housing unit having an outer surface and an inner surface forming a cavity therein;

a discharge port having an inner side end and an outer side end, said discharge port providing a first passageway from said cavity through said outer surface;

a return air port providing a second passageway from said outer surface to said cavity;

an air conditioning unit mounted in said inner cavity and fluidly coupled to said inner side end of said discharge port available for discharging conditioned air through said discharge port;

said conditioned air being cooled;

an electrical cord available electrically coupled to said air conditioning unit, said electrical cord adapted to be releasably coupled to an external power supply for operation of said air conditioning unit;

an extendable attachment means mounted on said outer surface of said housing for extending substantially parallel with said discharge port and defining a spacial area for directed distribution of conditioned air.

2. The portable suitcase air conditioner according to claim 1 including a thermostat for maintaining conditioned air passed through said discharge port at a predetermined temperature.

3. The portable suitcase air conditioner according to claim 1 wherein said conditioned air is heated.

4. The portable suitcase air conditioner according to claim 1 wherein said air conditioner unit includes a compressor containing a refrigerant, a hot side portion and a cool side portion, a first and second propeller fan driven by a single motor, said fan situated in front of said hot side portion and said second fan situated in front of said cool side portion.

5. The portable suitcase air conditioner according to claim 1 including a fan positioned to expel conditioned air through said discharge port.

6. The portable suitcase air conditioner according to claim 1 wherein said attachment means includes telescoped poles pivotally mounted on said housing unit in a stored position, the length of said telescoped poles in the stored position being substantially the same as said housing, said telescoped poles adapted to extend to a greater length and support a suitable material for forming an enclosure.

7. A portable air conditioner comprising:
   a housing unit defined as an enclosure having an outer surface and an inner surface forming a cavity therein;
   a discharge port having an inner side surface and an outer side surface, said discharge port providing a first passageway from said cavity to said outer surface;
   a return air port providing a second passageway from said outer surface to said cavity;
   an air conditioning unit mounted in said inner cavity and fluidly coupled to said inner side surface of said discharge port available for discharging conditioned air through said discharge port;
   said air conditioner unit includes a compressor containing a refrigerant, a hot side portion and a cool side portion, a first and second propeller fan driven by a single motor, said first fan situated in front of said hot side portion and said second fan situated in front of said cool side portion;
   said conditioned air being cooled;
   an electrical cord available electrically coupled to said air conditioning unit, said electrical cord adapted to be releasably coupled to an external power supply for operation of said air conditioning unit;
   attachment means securable to said outer side surface of said discharge port, said attachment available for covering a spacial area for directed distribution of conditioned air;
   wherein fan directional rotation is reversible.

8. A portable suitcase air conditioner comprising:
   a suitcase housing unit having an outer surface and an inner surface forming a cavity therein;
   a discharge port having an inner side end and an outer side end, said discharge port providing a first passageway from said cavity through said outer surface;
   a return air port providing a second passageway from said outer surface to said cavity;
   an air conditioning unit mounted in said inner cavity and fluidly coupled to said inner side end of said discharge port available for discharging conditioned air through said discharge port;
   means for maintaining conditioned air at a predetermined temperature;
   means for expelling conditioned air through said discharge port;
   an electrical cord available electrically coupled to said air conditioning unit, said electrical cord adapted to be releasably coupled to an external power supply for operation of said air conditioning unit;
   an attachment including telescoped poles pivotally mounted on said outer surface of said housing unit, said telescoped poles having a stored length substantially the same as said housing unit, said telescoped poles having an extended length adapted to support a flexible sheet of material covering a spacial area for directed distribution of conditioned air.

9. The portable suitcase air conditioner according to claim 8 wherein conditioned air is cooled.

10. The portable suitcase air conditioner according to claim 8 wherein conditioned air is heated.

11. The portable suitcase air conditioner according to claim 8 wherein said suitcase housing is a split housing to facilitate maintenance.

* * * * *